US010466205B2

(12) United States Patent
Brenner et al.

(10) Patent No.: US 10,466,205 B2
(45) Date of Patent: Nov. 5, 2019

(54) METHOD FOR DETERMINING MECHANICAL DAMAGE TO A ROTOR BLADE OF A WIND TURBINE

(71) Applicants: Daniel Brenner, Dresden (DE); Dirk Schollbach, Dresden (DE)

(72) Inventors: Daniel Brenner, Dresden (DE); Dirk Schollbach, Dresden (DE)

(73) Assignee: Weidmüller Monitoring Systems GmbH, Dresden (DE)

( * ) Notice: Subject to any disclaimer, the term of this patent is extended or adjusted under 35 U.S.C. 154(b) by 337 days.

(21) Appl. No.: 14/354,189

(22) PCT Filed: Oct. 10, 2012

(86) PCT No.: PCT/EP2012/004234
§ 371 (c)(1),
(2) Date: Sep. 12, 2014

(87) PCT Pub. No.: WO2013/060420
PCT Pub. Date: May 2, 2013

(65) Prior Publication Data
US 2015/0000404 A1 Jan. 1, 2015

(30) Foreign Application Priority Data
Oct. 26, 2011 (DE) .................. 10 2011 116 961

(51) Int. Cl.
*G01N 29/12* (2006.01)
*G01H 1/04* (2006.01)
(Continued)

(52) U.S. Cl.
CPC .............. *G01N 29/14* (2013.01); *F03D 17/00* (2016.05); *G01N 29/12* (2013.01);
(Continued)

(58) Field of Classification Search
CPC ...... F05B 227/334; G01N 29/12; G01H 1/06; G01H 1/14; G01H 3/04; G01H 3/06;
(Continued)

(56) References Cited

U.S. PATENT DOCUMENTS

2010/0209243 A1* 8/2010 Birkemose ............ F03D 7/0296
416/1
2011/0125419 A1* 5/2011 Bechhoefer ............ F03D 7/047
702/34

FOREIGN PATENT DOCUMENTS

DE 100 65 314 B4 8/2007
WO 2006/012827 A1 2/2006
(Continued)

OTHER PUBLICATIONS

International Search Report corresponding to PCT Application No. PCT/EP2012/004234, dated May 10, 2013 (German and English language document) (7 pages).

*Primary Examiner* — Herbert K Roberts
(74) *Attorney, Agent, or Firm* — Maginot, Moore & Beck LLP

(57) ABSTRACT

A method for detecting mechanical damage to a rotor blade of a wind turbine includes measuring vibrations of the rotor blade and generating a frequency-dependent vibration signal. A value of the signal energy over a predetermined frequency range of the vibration signal is determined at each of a number of measuring times and the respectively determined signal energy values are evaluated with respect to time in order to detect mechanical damage.

13 Claims, 3 Drawing Sheets

(51) Int. Cl.
*G01H 1/06* (2006.01)
*G01H 3/08* (2006.01)
*F03D 17/00* (2016.01)
*G01N 29/14* (2006.01)

(52) U.S. Cl.
CPC .............. *F05B 2270/334* (2013.01); *G01N 2291/014* (2013.01); *G01N 2291/0289* (2013.01)

(58) Field of Classification Search
CPC ........... G01H 3/08; Y02E 10/72; Y02E 10/74; Y02E 10/721
See application file for complete search history.

(56) References Cited

FOREIGN PATENT DOCUMENTS

| WO | 2007/131489 A1 | 11/2007 | |
|---|---|---|---|
| WO | 2009/047121 A2 | 4/2009 | |
| WO | WO 2009047121 A2 * | 4/2009 | ........... F03D 1/0658 |
| WO | 2011/029439 A1 | 3/2011 | |

* cited by examiner

METHOD FOR DETERMINING MECHANICAL DAMAGE TO A ROTOR BLADE OF A WIND TURBINE

This application is a 35 U.S.C. § 371 National Stage Application of PCT/EP2012/004234, filed on Oct. 10, 2012, which claims the benefit of priority to Serial No. DE 10 2011 116 961.3, filed on Oct. 26, 2011 in Germany, the disclosures of which are incorporated herein by reference in their entirety.

BACKGROUND

The present disclosure relates to a method for determining mechanical damage to a rotor blade of a wind turbine, a computing unit for executing the method, and a correspondingly set up monitoring means.

It is an essential prerequisite for the economic efficiency of wind turbines that, as far as possible, they operate without interruption. In particular, unplanned interruptions of operation due to damage to the drive train or, in particular, to the rotor blades, generate substantial repair costs and frequently result in insurance claims.

To avoid such disadvantages, it is frequently the case with wind turbines that a so-called condition-oriented maintenance is provided, which is effected, for example, on the basis of a vibration-based condition monitoring (CM) of rotor blades in corresponding condition monitoring devices or systems (condition monitoring systems, CMS). Such measures allow early identification of, for example, particular damage in rotor blades. CMS are frequently set up for remote diagnosis, wherein the condition messages are evaluated in certified diagnostic centers, frequently by specially trained personnel.

The use of CMS makes it possible to identify faults at an early stage, avoid unplanned downtimes and reduce costs for stocking of reserve parts, maintenance and production failures. Overall, the availability and production stability are increased as a result.

Known from DE 100 65 314 B4 and WO 2006/012827 A1, for monitoring the condition of rotor blades, are methods and devices in which a structure-borne sound is measured by means of one or more movement sensors disposed on the rotor blades, a frequency spectrum is determined from corresponding signals, by means of appropriate methods, in an evaluation unit, the frequency spectrum is compared with the reference spectra, stored in the evaluation unit, that correspond to defined damage states and special states, and the condition of the rotor blades is determined therefrom. As a result of this, it is intended, inter alia, that the occurrence of localized internal and external damage, and special states of the rotor blades that cause damage, for example extraordinary load situations, can be identified and assessed at an early stage, in order that the operation of the wind turbine can be influenced, preferably in an automated manner. WO 2007/131489 discloses an evaluation of corresponding sensor signals over time, and division of damage events into damage classes.

These methods are found to be insufficient, however, in particular for early identification of lightning damage. There is therefore a requirement for a more reliable prediction and/or identification of corresponding damage.

SUMMARY

Against this background, the disclosure proposes a method for determining mechanical damage to a rotor blade of a wind turbine, a computing unit for executing the method, and a corresponding monitoring means, having the features of the disclosure. Preferred designs constitute subject-matter of the dependent claims and of the following description.

The present disclosure is based on the unexpected insight that an evaluation of rotor blade spectra, i.e. frequency spectra, that have been generated from sensor signals from rotor blade sensors, in a predefined frequency range (for example, above 100 or 200 Hz), permits an early diagnosis of incipient damage in rotor blades. Such a diagnosis is not possible by means of a conventional evaluation of rotor blade sensors. This relates, in particular, to mechanical damage, which influences the construction of the rotor blade, such as, for example, cracks or lightning damage, in which parts of a rotor blade, which are usually laminated or adhesive bonded, become damage and/or partially separated. Such damage causes manifestly high-frequency vibrations, which, advantageously however, are not detected in the form of discrete frequencies but, in particular, have diagnostic value in the form of an averaged signal energy, over a defined frequency range.

In other words, in rotor blade spectra above 100 Hz or 150 Hz, in particular above 200 Hz, for example in a range from 100 to 500 Hz or from 150 to 500 Hz or 1000 Hz, such damage, in particular lightning damage, exhibits differences from the spectra of undamaged rotor blades. Frequencies are preferably those from the lower low-frequency range, i.e. from approximately 20 Hz to approximately 5 kHz.

As a result of this, particular damage, in particular constructional damage, can be identified at an early stage, thereby making it possible to rectify the damage at an early stage and, in particular, in a planned manner. This enables the operator of a corresponding wind turbine to realize significant cost savings, and increases the safety and availability of the wind turbine. Such a more timely and more reliable damage detection makes it possible to form a proposition concerning the progression of initially relatively small, nascent or incipient damage, and thus concerning the urgency of a repair.

The disclosure proposes that, for a rotor blade, preferably for each rotor blade, a measure of signal energy over a specific frequency range such as, for example, the previously explained frequency range of from 150 to 500 Hz, be determined and evaluated with respect to time. Damage may be inferred from the time characteristic. For example, for the evaluation, the differences may be determined for the individual rotor blades relative to each other, or a difference in relation to a reference value may be determined. A comparative consideration of the individual rotor blades is the obvious choice, because this makes it possible to exclude factors that affect all rotor blades simultaneously, such as, for example, high-frequency superpositions due to drive train influences and/or wind-induced frequencies.

The consideration according to the disclosure is effected intermittently or (quasi-) continuously over a specific observation time. The evaluation of the signal energy measure can be effected over a corresponding time period, wherein, in particular, specific time portions can be integrated, averaged or specified in the form of a sliding average.

Preferably, the signal energy itself is determined as a signal energy measure over the determined frequency range, in particular by integration of the signal intensity over the frequency range. Further, preferably, a difference between the signal energy and a signal-energy mean value over a plurality of rotor blades or all rotor blades, or a reference value, may be formed as a signal energy measure. The representation of the difference of the signal energy of the individual rotor blade spectra in relation to a common mean value of all three blades or in relation to a reference value provides early indication of damage in the time trend characteristic.

As an alternative or in addition to a comparative consideration of rotor blades, spectra of individual rotor blades may also be normalized in respect of the influences of differing operating parameters, such that the characteristic of the normalized mean signal energy of an individual rotor blade is sufficient for assessment. This means that, for an evaluation according to the disclosure, there does not necessarily have to be a comparison of all rotor blades. This may be desirable, because a damaging event may occur, not just on one rotor blade but, for example, on two of three rotor blades. For example, if there is lightning damage on two rotor blades, this could result in these two rotor blades being found to be similar in their spectral behavior, i.e. exhibiting differences in the frequency range mentioned. These differences, if considered in comparison with the third, undamaged, rotor blade, might possibly result in misleading propositions being formed in respect of this third, undamaged, rotor blade.

A particular advantage of the disclosure consists in that the characteristic of the signal energy measure, or of the signal energy, over the stated frequency range, or of a difference, exhibits a correlation with a damage intensity. This makes it possible to deduce a damage intensity from the characteristic of the signal energy measure, such that the progression of a damage can be detected and, for example, if a defined threshold value is exceeded, measures can be initiated.

Overall, the present disclosure thus enables damage to rotor blades of a wind turbine to be detected at an earlier stage and more reliably. In particular, as mentioned, the disclosure allows early identification of constructional damage such as cracks, hair cracks and lightning damage, before these can be detected, at an advanced stage, by conventional methods.

It is particularly advantageous, in the scope of the present disclosure, to use capacitive acceleration sensors as vibration sensors. By means of such capacitive sensors, it is possible to determine a lower limit frequency of 0 Hz, such that, for example, slowly rotating components can also additionally be monitored in a safe and reliable manner. In the case of such sensors it is obvious, in respect of improved monitoring of rapidly rotating components, to extend the frequency range upward. Corresponding sensors thus allow better monitoring than with usually installed piezoelectric acceleration sensors, with which only a frequency range of between approximately 0.1 Hz and 500 Hz can be evaluated.

Advantageously, for rotor blade monitoring, it is possible to use commercially available blade monitoring means that have, for example, biaxial acceleration sensors in each rotor blade, which are positioned at a distance of approximately one third of the blade length in relation to the blade root. In the working position, a corresponding sensor measures the acceleration tangentially in relation to the rotor rotation, and the acceleration in the direction of the rotor axis (tangential and axial acceleration).

Advantageously, in the scope of the present disclosure, the evaluation of corresponding frequencies is effected in the form of frequency spectra that are generated by means of Fourier transformation, for example from acceleration data of corresponding sensors. The frequency spectra may also be generated differently, e.g. by means of discrete cosine transformation, wavelet transformation or ARMA (autoregressive moving average) spectral estimators.

The previously explained advantages relate likewise to the method according to the disclosure, the monitoring means according to the disclosure, and to the corresponding computing unit, which, in particular in respect of programming, is set up to execute a method according to the disclosure.

Moreover, the implementation of the disclosure in the form of software is advantageous, since this enables costs to be kept particularly low, in particular if an executing computing unit is also used for additional tasks such as, for example, controlling a wind turbine, or as a CMS, and is therefore present in any case. Suitable data media for provision of the computer program are, in particular, diskettes, hard drives, flash memories, EEPROMs, CD ROMs, DVDs, and other media. It is also possible for a program to be downloaded via computer networks (Internet, intranet, etc.).

Further advantages and designs of the disclosure are given by the description and the accompanying drawings.

It is understood that the aforementioned features and those yet to be explained in the following are applicable, not only in the respectively stated combination, but also in other combinations or singly, without departure from the scope of the present disclosure.

The disclosure is represented schematically in the drawings on the basis of an exemplary embodiment, and is described in detail in the following with reference to the drawings.

DETAILED DESCRIPTION

Figure 1:
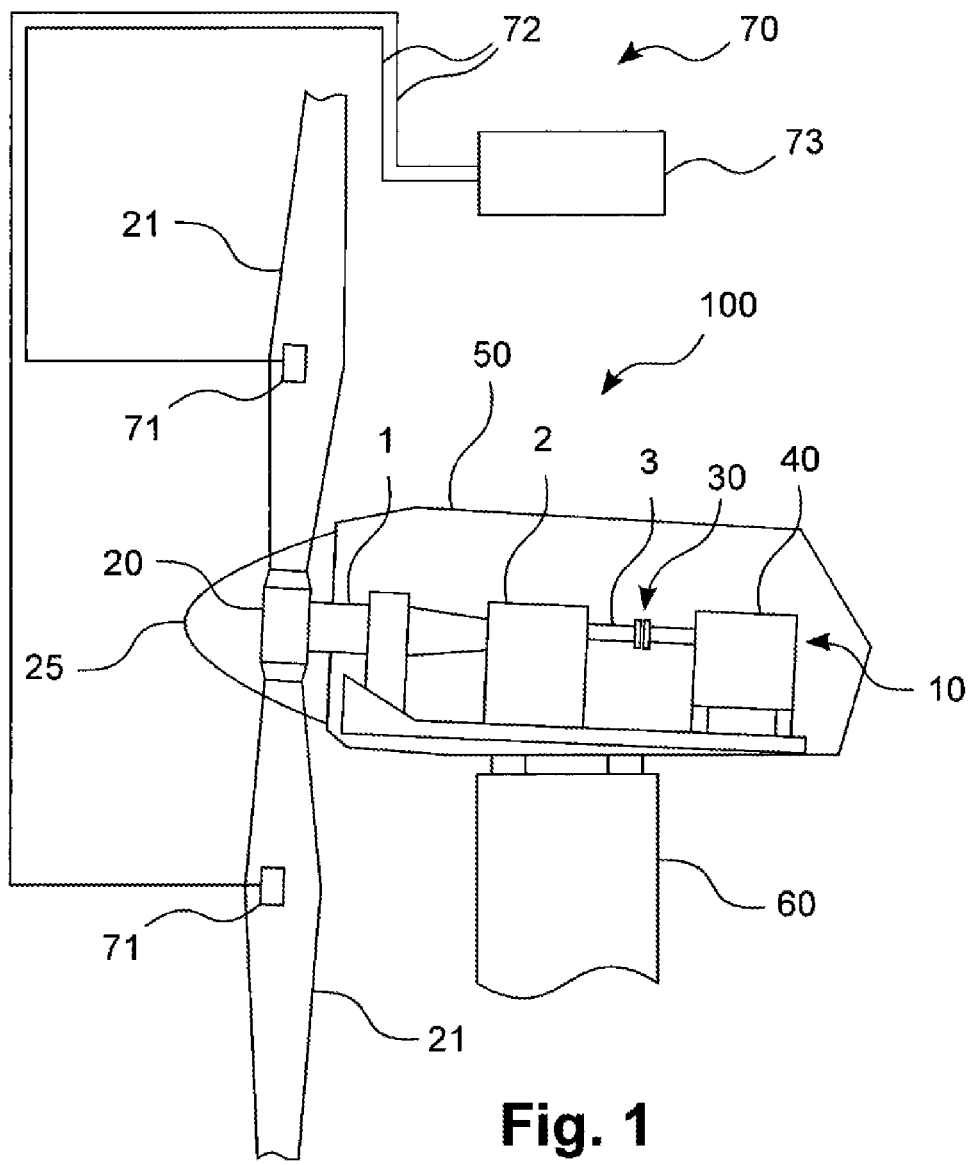
FIG. 1 shows a wind turbine, which can be monitored by means of a method according to an embodiment of the disclosure.

Represented in FIG. 1 is a longitudinal sectional view of a part of a wind turbine, which can be monitored by means of a method according to a particularly preferred embodiment of the disclosure. The wind turbine is denoted as a whole by 100, its drive train 10 being denoted by 10.

The drive train 10 shown is composed substantially of a main shaft 1, to which a rotor 20 is attached, and of a gearbox 2 and a generator shaft 3. The gearbox 2 may be, for example, a three-stage gearbox normally used in wind turbines. The main shaft 1 is connected by force closure to the rotor 20, for example a rotating blade rotor. The generator shaft 3 may be connected to a generator 40 via a clutch 30. The main shaft 1, the gearbox 2, the generator shaft 3 and the generator 40 are supported with corresponding means, enclosed in a housing 50 and mounted on a tower 60. Two rotor blades 21, represented partially, are shown on the rotor 20. Rotors normally used in wind turbines have, for example, three blades 21. The disclosure is equally applicable in gearless wind turbines.

The blades 21 of the rotor 20 have acceleration sensors 71, which are disposed, for example, at a distance of one third of the blade length in relation to a rotor hub, or rotor axis, 25. The acceleration sensors 71, as part of an evaluation system 70, are connected by means of lines 72 to an evaluation means 73, which evaluates the signals of the acceleration sensors 71, and which for this purpose may have a computing unit, not represented. The acceleration sensors 71 may each have two one-dimensional acceleration sensors having mutually differing directions of acceleration, by means of which an acceleration in the swing direction of the blade, and thus tangentially in relation to the rotor, and in the strike direction of the blade, i.e. axially in relation to the rotor, can be sensed.

Figure 2:
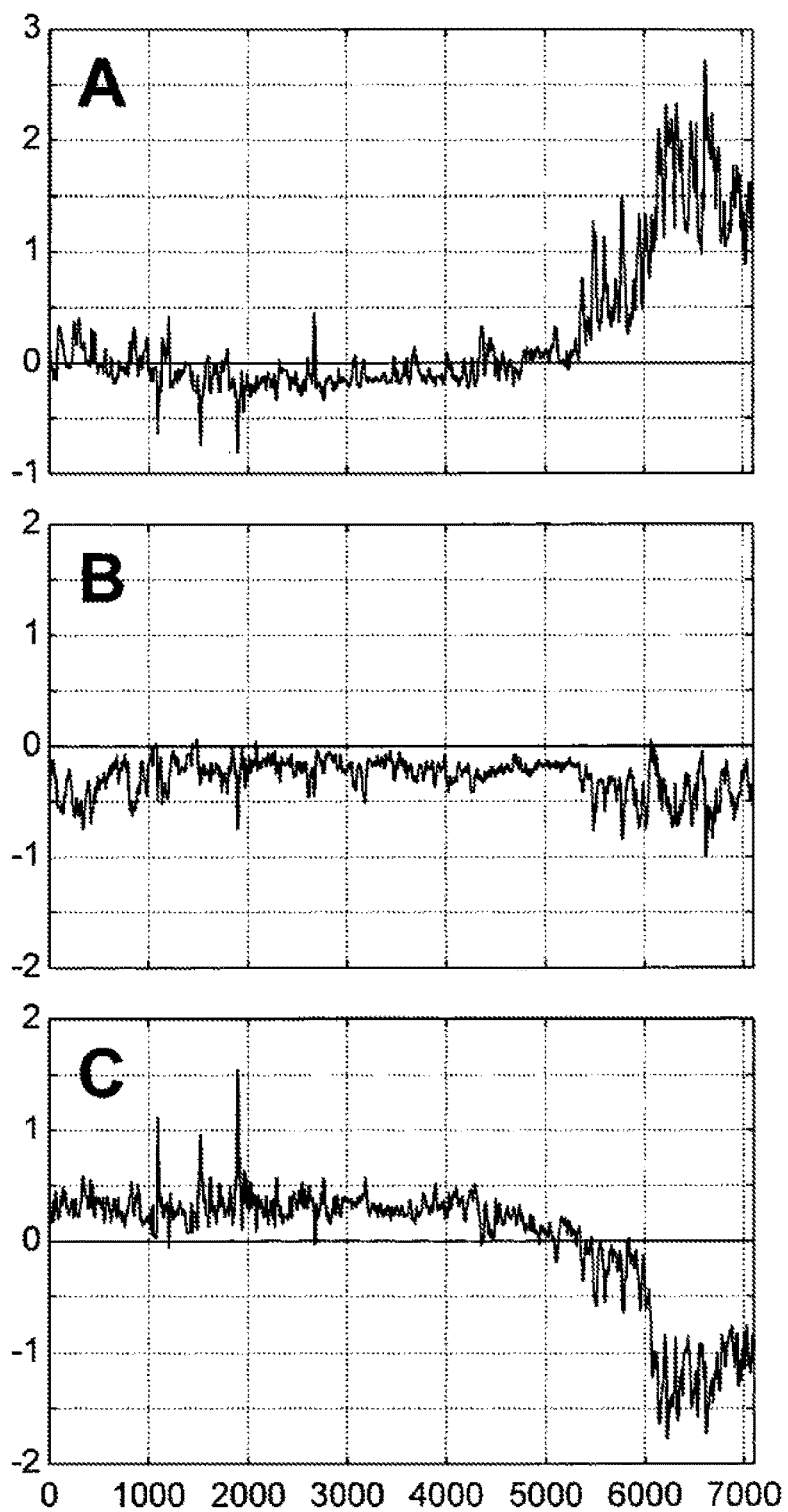
FIG. 2 shows a time characteristic of a frequency signal energy in a first rotor blade direction, obtained according to a particularly preferred embodiment of the disclosure.
Figure 3:
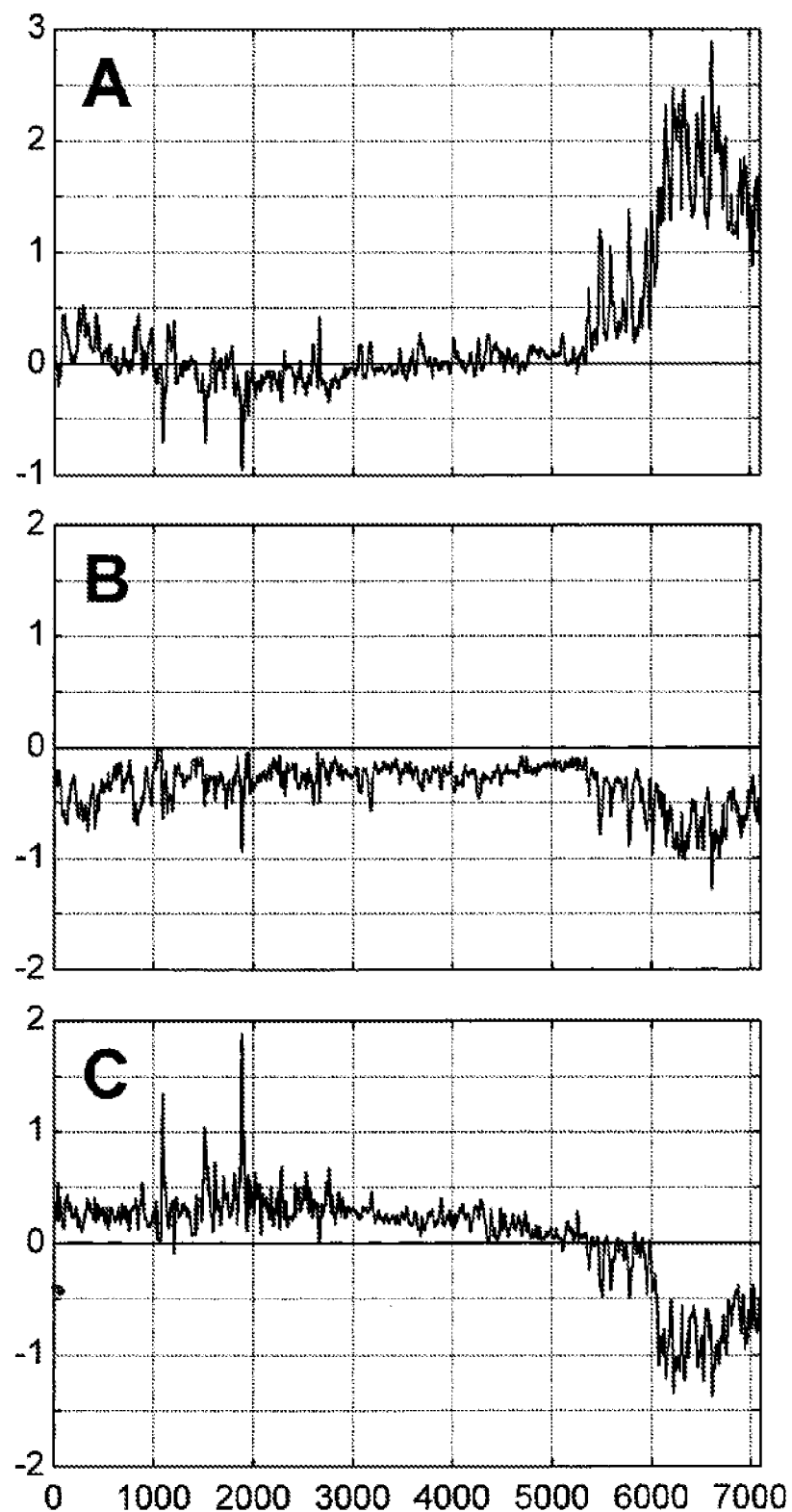
FIG. 3 shows a time characteristic of a frequency signal energy in a second rotor blade direction, obtained according to a particularly preferred embodiment of the disclosure.

FIGS. 2 and 3 each show three plotted signal energy measures, of which each is assigned to a rotor blade of a wind turbine having three rotor blades. A signal energy is determined for each rotor blade, averaged over the same frequency range. Furthermore, a mean value of these three signal energies is determined. As a signal energy measure for a specific rotor blade, the present example uses a difference between the signal energy for this specific rotor blade, averaged over the frequency range, and the mean value. A frequency range of from 150 to 350 Hz was used. The signal energy measures are plotted as trend characteristics A, B, C over a time period on the abscissa.

Indicated on the abscissa in this case is the so-called BAID (a measurement cycle identification). A measurement is stored, e.g. on a data backup server, per hour in the monitoring means used, such that the BAID 7000 corresponds to approximately 10 months of measurement time. The trend development over time is recorded.

The signal energy measure used here, i.e. the difference between signal energy and the mean value over the frequency range concerned, shows a variation and damage more clearly and in a more timely manner than the representation of the absolute value of the signal energy.

FIG. 2 shows a time characteristic in the swing direction, obtained according to a particularly preferred embodiment of the disclosure. FIG. 3, in a manner corresponding to FIG. 2, shows an evaluation in the strike direction.

It is evident that the signal energy measure A, both in the swing direction and in the strike direction, has a significantly higher amplitude from approximately BAID 6000 onwards than for the period of time before an incident of damage (e.g. BAID 5000). The signal energy measure A is also higher in comparison with the other two characteristics B and C, i.e. the other blades. The signal energy measure A for the rotor blade A increases steadily in both measurement directions from approximately six weeks before the represented end of the measurement period.

A rotor blade inspection revealed damage caused by lightning strike, in which the blade tip had been torn open. In addition, there were small transverse cracks close to the lightning strike. It is to be assumed that, as it rotates, the torn blade tip generates shock pulses caused by the parts striking against each other.

The invention claimed is:

1. A method for identifying mechanical damage to a rotor blade of a wind turbine, comprising:
    sensing vibrations of the rotor blade with an acceleration sensor;
    generating a frequency-dependent vibration signal corresponding to the sensed vibrations for a predefined frequency range with a computing unit operably connected to the acceleration sensor;
    integrating the frequency-dependent vibration signal over the predefined frequency range for a plurality of measurement instants to determine a signal energy measure for each measurement instant of the plurality of measurement instants with the computing unit; and
    identifying mechanical damage in the rotor blade by (i) determining a damage intensity based on the respectively determined signal energy measures and comparing the damage intensity to a defined first threshold value with the computing unit, and (ii) comparing the respectively determined signal energy measures with corresponding signal energy measures of another rotor blade of the same wind turbine, and determining that a difference between time characteristics of the two signal energy measures exceeds a corresponding second threshold value,
    wherein the predefined frequency range includes frequencies above 50 Hz and below 1000 Hz.

2. The method as claimed in claim 1, wherein the predefined frequency range has a width of at least 50 Hz.

3. The method as claimed in claim 1, wherein a frequency range of 150 Hz to 1000 Hz is used as the predefined frequency range.

4. The method as claimed in claim 1, further comprising:
    forming a difference between the respectively determined signal energy measures and a mean signal energy in the predefined frequency range; and
    identifying the mechanical damage in the rotor blade based on the formed difference.

5. The method as claimed in claim 1, wherein:
    identifying the mechanical damage in the rotor blade further comprises comparing the respectively determined signal energy measures of the rotor blade with a mean value, over corresponding signal energy measures, of at least two rotor blades of the same wind turbine, and
    the computing unit identifies the mechanical damage if a difference between time characteristics of the respectively determined signal energy measures and the mean value exceeds a corresponding third threshold value.

6. The method as claimed in claim 1, wherein:
    identifying the mechanical damage in the rotor blade further comprises comparing the respectively determined signal energy measures of the rotor blade with a reference value, and
    the computing unit identifies the mechanical damage if a difference between time characteristics of the respectively determined signal energy measures and the reference value exceeds a corresponding third threshold value.

7. The method as claimed in claim 1, wherein the predefined frequency range includes frequencies above 100 Hz.

8. The method as claimed in claim 1, wherein the predefined frequency range includes frequencies below 500 Hz.

9. The method as claimed in claim 1, wherein:
    identifying the mechanical damage in the rotor blade further comprises comparing the respectively determined signal energy measures of the rotor blade with a mean value, over corresponding signal energy measures, of all rotor blades of the same wind turbine, and
    the computing unit identifies the mechanical damage if a difference between time characteristics of the respectively determined signal energy measures and the mean value exceeds a corresponding third threshold value.

10. The method as claimed in claim 1, wherein the acceleration sensor is mounted on the rotor blade.

11. The method as claimed in claim 1, wherein the measurement instants of the plurality of measurement instants are each spaced apart in time.

12. A computing unit, configured to execute a method for identifying mechanical damage to a rotor blade of a wind turbine, the method comprising:

sensing vibrations of the rotor blade with an acceleration sensor operably connected to the computing unit;

generating a frequency-dependent vibration signal corresponding to the sensed vibrations for a predefined frequency range with the computing unit;

integrating the frequency-dependent vibration signal over the predefined frequency range for a plurality of measurement instants to determine a signal energy measure for each measurement instant of the plurality of measurement instants with the computing unit; and identifying mechanical damage in the rotor blade by (i) determining a damage intensity based on the respectively determined signal energy measures and comparing the damage intensity to a defined first threshold value with the computing unit, and (ii) comparing the respectively determined signal energy measures with corresponding signal energy measures of another rotor blade of the same wind turbine, and determining that a difference between time characteristics of the two signal energy measures exceeds a corresponding second threshold value, wherein the predefined frequency range includes frequencies above 50 Hz and below 1000 Hz.

13. A monitoring device for at least one rotor blade of a wind turbine, comprising:

at least one vibration sensor configured to sense vibrations of the rotor blade; and a computing unit operably connected to the at least one vibration sensor and configured to execute a method for identifying mechanical damage to the rotor blade, the method comprising:

sensing vibrations of the rotor blade with the at least one vibration sensor;

generating a frequency-dependent vibration signal corresponding to the sensed vibrations for a predefined frequency range with the computing unit;

integrating the frequency-dependent vibration signal over the predefined frequency range for a plurality of measurement instants to determine a signal energy measure for each measurement instant of the plurality of measurement instants with the computing unit; and identifying mechanical damage in the rotor blade by (i) determining a damage intensity based on the respectively determined signal energy measures and comparing the damage intensity to a defined first threshold value with the computing unit, and (ii) comparing the respectively determined signal energy measures with corresponding signal energy measures of another rotor blade of the same wind turbine, and determining that a difference between time characteristics of the two signal energy measures exceeds a corresponding second threshold value, wherein the predefined frequency range includes frequencies above 50 Hz and below 1000 Hz.

\* \* \* \* \*